United States Patent  
Saulsbury et al.

(10) Patent No.: US 10,117,012 B2
(45) Date of Patent: Oct. 30, 2018

(54) WIRELESS EAR BUDS WITH PROXIMITY SENSORS

(71) Applicant: Apple Inc., Cupertino, CA (US)

(72) Inventors: Ashley N. Saulsbury, Saratoga, CA (US); Travis J. McQueen, San Jose, CA (US)

(73) Assignee: Apple Inc., Cupertino, CA (US)

( * ) Notice: Subject to any disclaimer, the term of this patent is extended or adjusted under 35 U.S.C. 154(b) by 12 days.

(21) Appl. No.: 15/270,445

(22) Filed: Sep. 20, 2016

(65) Prior Publication Data

US 2017/0094389 A1     Mar. 30, 2017

Related U.S. Application Data

(60) Provisional application No. 62/233,848, filed on Sep. 28, 2015.

(51) Int. Cl.
*H04R 1/10* (2006.01)
*A61B 5/00* (2006.01)
(52) U.S. Cl.
CPC ......... *H04R 1/1016* (2013.01); *A61B 5/6803* (2013.01); *A61B 5/6817* (2013.01); *H04R 1/1041* (2013.01); *H04R 2420/07* (2013.01)
(58) Field of Classification Search
CPC ........ H04R 25/00; H04R 25/60; H04R 25/65; H04R 2225/023; H04R 2225/025; H04R 2460/13; H04R 1/1016; H04R 1/105
USPC ................. 381/322, 324, 328, 330, 380–381
See application file for complete search history.

(56) References Cited

U.S. PATENT DOCUMENTS

| | | | |
|---|---|---|---|
| 6,754,358 B1 * | 6/2004 | Boesen | H04M 1/6066 |
| | | | 381/380 |
| 7,561,708 B2 | 7/2009 | Rohrlein | |
| 8,259,984 B2 * | 9/2012 | van der Bilt | H04R 1/1041 |
| | | | 381/380 |
| 8,805,452 B2 | 8/2014 | Lee | |
| 9,344,792 B2 | 5/2016 | Rundle | |
| (Continued) | | | |

FOREIGN PATENT DOCUMENTS

| | | |
|---|---|---|
| EP | 2451187 A2 | 5/2012 |
| EP | 2839675 A1 | 2/2015 |

OTHER PUBLICATIONS

Motorola Hint + Bluetooth Earbuds, motorolahome.com [online], retrieved Aug. 19, 2016 <URL:https://www.motorolastore.com/accessories/bluetooth-headsets/motorola-hint.html>.

(Continued)

*Primary Examiner* — Suhan Ni
(74) *Attorney, Agent, or Firm* — Treyz Law Group, P.C.; G. Victor Treyz

(57) ABSTRACT

Ear buds are provided that communicate wirelessly with an electronic device. To determine the current status of the ear buds and thereby take suitable action in controlling the operation of the electronic device and ear buds, the ear buds may be provided with sensor circuitry. The sensor circuitry may include proximity sensors. The ear buds may each have a housing with a main body portion that is configured to be inserted into the ear of the user and an elongated stem portion that extends from the main body portion. The proximity sensors may include sensors on the main body and sensors on the stem. The proximity sensors may be light-based sensors that emit light that passes through the housing.

18 Claims, 8 Drawing Sheets

(56) References Cited

U.S. PATENT DOCUMENTS

| | | | |
|---|---|---|---|
| 2009/0097689 A1* | 4/2009 | Prest | H04R 1/028 |
| | | | 381/380 |
| 2010/0087896 A1* | 4/2010 | McCreery | A61F 5/566 |
| | | | 607/62 |
| 2013/0279724 A1 | 10/2013 | Stafford et al. | |
| 2013/0322646 A1 | 12/2013 | Davie et al. | |
| 2014/0016803 A1 | 1/2014 | Puskarich | |
| 2015/0289818 A1 | 10/2015 | LeBoeuf et al. | |
| 2016/0050474 A1 | 2/2016 | Rye et al. | |

OTHER PUBLICATIONS

Moto Hint, Wireless Bluetooth Earbuds, Motorola [online], retrieved Sep. 28, 2016 <URL:https://www.motorola.com/us/accessories/talk/bluetooth-headsets/moto-hint/moto-hint-pdp.html>.

* cited by examiner

WIRELESS EAR BUDS WITH PROXIMITY SENSORS

This application claims the benefit of provisional patent application No. 62/233,848, filed Sep. 28, 2015, which is hereby incorporated by reference herein in its entirety.

BACKGROUND

This relates generally to electronic devices, and, more particular, to wearable electronic devices such as ear buds.

Cellular telephones, computers, and other electronic equipment may generate audio signals during media playback operations and telephone calls. Users often use microphones and speakers in these devices to handle telephone calls and media playback. Sometimes ear buds have cords that allow the ear buds to be plugged into an electronic device.

Wireless ear buds provide users with more flexibility than wired ear buds, but can be challenging to use. It is not always clear whether a wireless ear bud is located in a pocket, is resting on a table, or is in a user's ear. As a result, audio signals can sometimes be misdirected.

It would therefore be desirable to be able to provide improved wearable electronic devices such as improved wireless ear buds.

SUMMARY

Ear buds are provided that communicate wirelessly with an electronic device. The electronic device may be a cellular telephone, wristwatch device, or other electronic equipment. A wireless link may be established between the electronic device and the ear buds. The wireless link may be used to transfer audio information between the ear buds and the electronic device. For example, if the electronic device is being used for a cellular telephone call or media playback operations, audio associated with the cellular telephone call or media playback operations may be transferred between the electronic device and the ear buds over the wireless link.

The state of the ear buds may be monitored and corresponding actions taken in controlling the ear buds and electronic device. For example, if a user places an ear bud in the ear of the user in response to receiving a cellular telephone call with the electronic device, the telephone call can be automatically transferred to the ear bud. If the user removes the ear bud from the ear during a telephone call or media playback operation, the audio for the call or media playback operation can be routed to a speaker in the electronic device.

During use by a user, the ear buds may be stored in a case or pocket, may be rest on a table top, may be inserted into the ear of a user, or may rest in the ear of a user. To determine the current status of the ear buds and thereby take suitable action in controlling the operation of the electronic device and ear buds, the ear buds may be provided with sensor circuitry. The sensor circuitry may include proximity sensors. The ear buds may each have a main body portion that is configured to be inserted into the ear of the user and an elongated stem portion that extends from the main body portion. The proximity sensors may include sensors on the main body and sensors on the stem.

The proximity sensors may be light-based sensors each of which has a light source such as an infrared light-emitting diode and a corresponding light detector. Infrared light from the light-emitting diodes can pass through the housings of the ear buds. There may be two proximity sensors on the main body of each ear bud and two proximity sensors on the stem of each ear bud or other numbers of proximity sensors may be used.

DETAILED DESCRIPTION

An electronic device such as a host device may have wireless circuitry. Wireless wearable electronic devices such as wireless ear buds may communicate with the host device and with each other. In general, any suitable types of host electronic device and wearable wireless electronic devices may be used in this type of arrangement. The use of a wireless host such as a cellular telephone, computer, or wristwatch may sometimes be described herein as an example. Moreover, any suitable wearable wireless electronic devices may communicate wirelessly with the wireless host. The use of wireless ear buds to communicate with the wireless host is merely illustrative.

Figure 1:
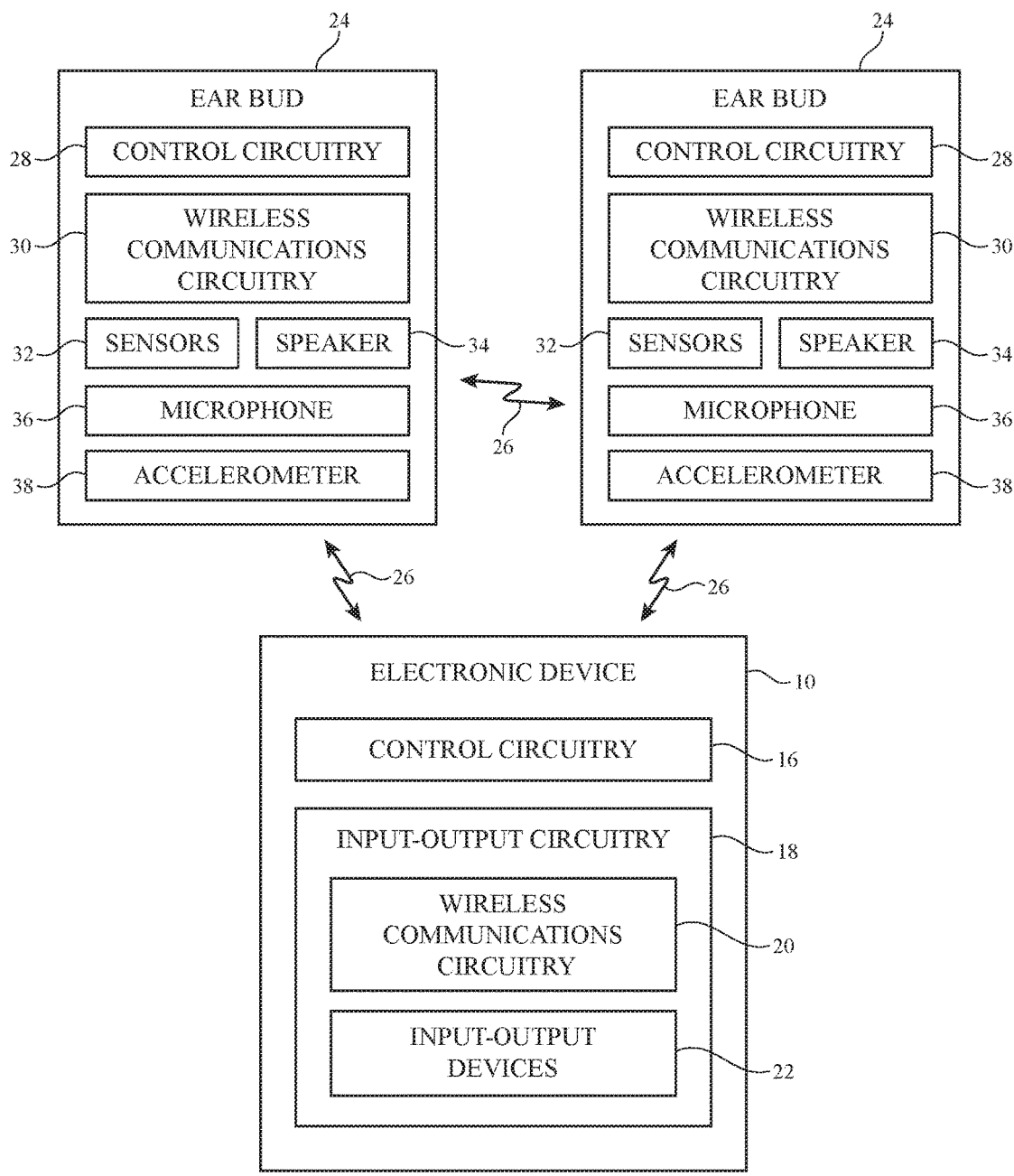
FIG. 1 is a schematic diagram of an illustrative system including electronic equipment that communicates wirelessly with wearable electronic devices such as wireless ear buds in accordance with an embodiment.

A schematic diagram of an illustrative system in which a wireless electronic device host communicates wirelessly with accessory devices such as ear buds is shown in FIG. 1. Host electronic device 10 may be a cellular telephone, may be a computer, may be a wristwatch device or other wearable equipment, may be part of an embedded system (e.g., a system in a plane or vehicle), may be part of a home network, or may be any other suitable electronic equipment. Illustrative configurations in which electronic device 10 is a watch, computer, or cellular telephone, may sometimes be described herein as an example.

As shown in FIG. 1, electronic device 10 may have control circuitry 16. Control circuitry 16 may include storage and processing circuitry for supporting the operation of device 10. The storage and processing circuitry may include storage such as hard disk drive storage, nonvolatile memory (e.g., flash memory or other electrically-programmable-read-only memory configured to form a solid state drive), volatile memory (e.g., static or dynamic random-access-memory), etc. Processing circuitry in control circuitry 16 may be used to control the operation of device 10. The processing circuitry may be based on one or more microprocessors, microcontrollers, digital signal processors, baseband processors, power management units, audio chips, application specific integrated circuits, etc.

Device 10 may have input-output circuitry 18. Input-output circuitry 18 may include wireless communications circuitry 20 (e.g., radio-frequency transceivers) for supporting communications with wireless wearable devices such as ear buds 24 or other wireless wearable electronic devices via wireless links 26. Ear buds 24 may have wireless communications circuitry 30 for supporting communications with circuitry 20 of device 10. Ear buds 24 may also communicate with each other using wireless circuitry 30. In general, the wireless devices that communicate with device 10 may be any suitable portable and/or wearable equipment. Configurations in which wireless wearable devices 24 are ear buds are sometimes described herein as an example.

Input-output circuitry in device 10 such as input-output devices 22 may be used to allow data to be supplied to device 10 and to allow data to be provided from device 10 to external devices. Input-output devices 22 may include buttons, joysticks, scrolling wheels, touch pads, key pads, keyboards, microphones, speakers, displays (e.g., touch screen displays), tone generators, vibrators (e.g., piezoelectric vibrating components, etc.), cameras, sensors, light-emitting diodes and other status indicators, data ports, etc. A user can control the operation of device 10 by supplying commands through input-output devices 22 and may receive status information and other output from device 10 using the output resources of input-output devices 22. If desired, some or all of these input-output devices may be incorporated into ear buds 24.

Each ear bud 24 may have control circuitry 28 (e.g., control circuitry such as control circuitry 16 of device 10), wireless communications circuitry 30 (e.g., one or more radio-frequency transceivers for supporting wireless communications over links 26), may have one or more sensors 32, and may have additional components such as speakers 34, microphones 36, and accelerometers 38. Speakers 34 may play audio into the ears of a user. Microphones 36 may gather audio data such as the voice of a user who is making a telephone call. Accelerometer 38 may detect when ear buds 24 are in motion or are at rest.

Control circuitry 28 on ear buds 24 and control circuitry 16 of device 10 may be used to run software on ear buds 24 and device 10, respectively. During operation, the software running on control circuitry 28 and/or 16 may be used in gathering sensor data, user input, and other input and may be used in taking suitable actions in response to detected conditions. As an example, control circuitry 28 and 16 may be used in handling audio signals in connection with incoming cellular telephone calls when it is determined that a user has placed one of ear buds 24 in the ear of the user. Control circuitry 28 and/or 16 may also be used in coordinating operation between a pair of ear buds 24 that are paired with a common host device (e.g., device 10), handshaking operations, etc.

In some situations, it may be desirable to accommodate stereo playback from ear buds 24. This can be handled by designating one of ear buds 24 as a primary ear bud and one of ear buds 24 as a secondary ear bud. The primary ear bud may serve as a slave device while device 10 serves as a master device. A wireless link between device 10 and the primary ear bud may be used to provide the primary ear bud with stereo content. The primary ear bud may transmit one of the two channels of the stereo content to the secondary ear bud for communicating to the user (or this channel may be transmitted to the secondary ear bud from device 10). Microphone signals (e.g., voice information from the user during a telephone call) may be captured by using microphone 36 in the primary ear bud and conveyed wirelessly to device 10.

Sensors 32 may include strain gauge sensors, proximity sensors, ambient light sensors, touch sensors, force sensors, temperature sensors, pressure sensors, magnetic sensors, accelerometers (see, e.g., accelerometers 38), gyroscopes and other sensors for measuring orientation (e.g., position sensors, orientation sensors), microelectromechanical systems sensors, and other sensors. Proximity sensors in sensors 32 may emit and/or detect light and/or may be capacitive proximity sensors that generate proximity output data based on measurements by capacitance sensors (as examples). Proximity sensors may be used to detect the presence of a portion of a user's ear to ear bud 24 and/or may be triggered by the finger of a user (e.g., when it is desired to use a proximity sensor as a capacitive button or when a user's fingers are gripping part of ear bud 24 as ear bud 24 is being inserted into the user's ear).

Figure 2:
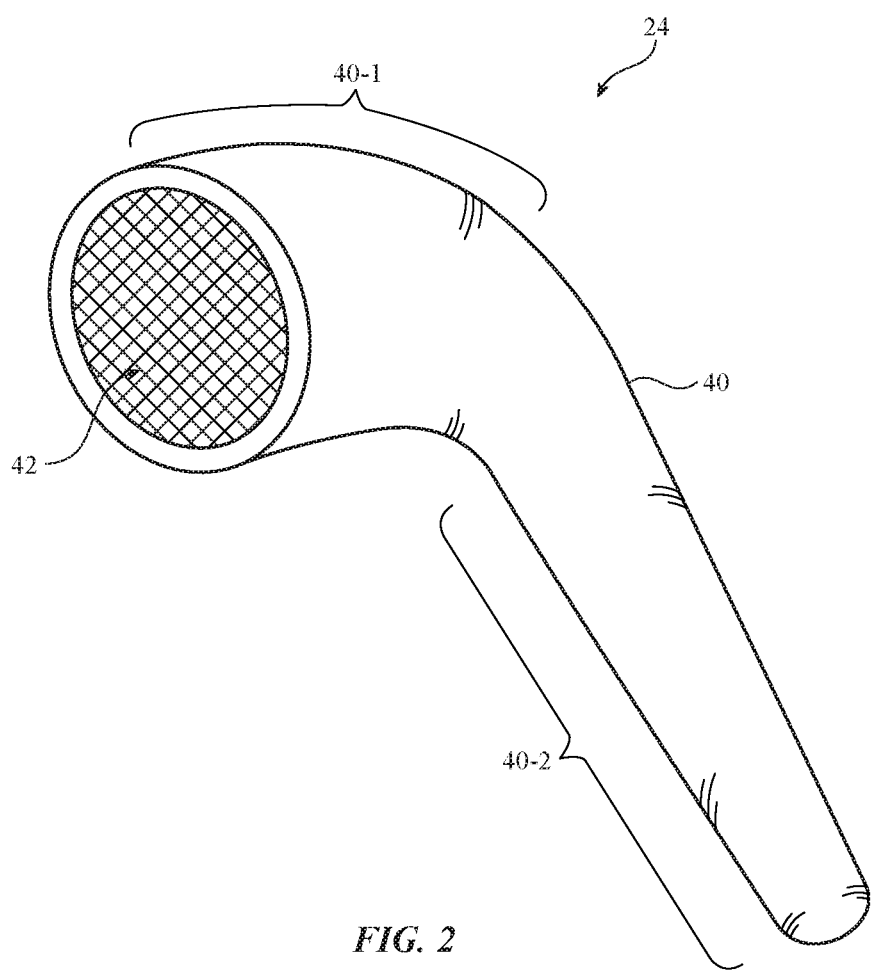
FIG. 2 is a perspective view of an illustrative ear bud in accordance with an embodiment.

FIG. 2 is a perspective view of an illustrative ear bud. As shown in FIG. 2, ear bud 24 may include a housing such as housing 40. Housing 40 may have walls formed from plastic, metal, ceramic, glass, sapphire or other crystalline materials, fiber-based composites such as fiberglass and carbon-fiber composite material, natural materials such as wood and cotton, other suitable materials, and/or combinations of these materials. Housing 40 may have a main portion such as main body 40-1 that houses audio port 42 and a stem portion such as stem 40-2 or other elongated portion that extends away from main body portion 40-1. During operation, a user may grasp stem 40-2 and, while holding stem 40-2, may insert main portion 40-1 and audio port 42 into the ear.

Audio ports such as audio port 42 may be used for gathering sound for a microphone and/or for providing sound to a user (e.g., audio associated with a telephone call, media playback, an audible alert, etc.). For example, audio port 42 of FIG. 2 may be a speaker port that allows sound from speaker 34 (FIG. 1) to be presented to a user. Sound may also pass through additional audio ports (e.g., one or more perforations may be formed in housing 40 to accommodate microphone 36).

Figure 3:
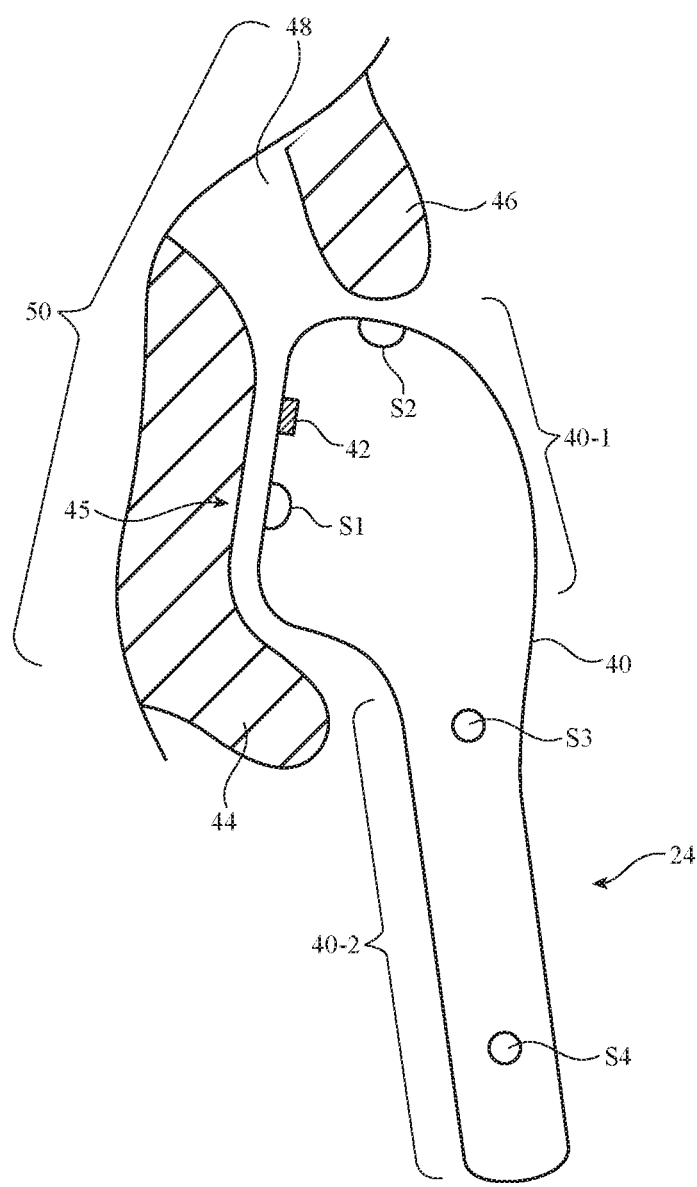
FIG. 3 is a side view of an illustrative ear bud located in an ear of a user in accordance with an embodiment.

Sensor data (e.g., proximity sensor data, accelerometer data or other motion sensor data), wireless communications circuitry status information, and/or other information may be used in determining the current operating state of each ear bud 24. Proximity sensor data may be gathered using proximity sensors located at any suitable locations in housing 40. FIG. 3 is a side view of ear bud 24 in an illustrative configuration in which ear bud 24 has four proximity sensors S1, S2, S3, and S4. Sensors S1 and S2 may be mounted in main body portion 40-1 of housing 40 and sensors S3 and S4 may be mounted on stem 40-2 or other mounting arrangements may be used. In the example of FIG. 3, there are four proximity sensors on housing 40. More proximity sensors or fewer proximity sensors may be used in ear bud 24, if desired.

Sensors S1, S2, S3, and S4 may use reflected light, capacitance measurements, or other measurements to determine whether an external object is nearby. During operation, a raw sensor signal (e.g., a reflected light signal, capacitance signal, etc.) may be compared to a predetermined threshold. If the raw signal is greater than the threshold, the sensor output will be positive (i.e., an external object is in the vicinity of the sensor). If the raw signal is less than the threshold of the sensor, the sensor output will be negative (i.e., no external object is in the vicinity of the sensor).

As shown in FIG. 3, ear bud 24 may be inserted into the ear (ear 50) of a user, so that speaker port 42 is aligned with ear canal 48. Ear 50 may have features such as concha 46, tragus 45, and antitragus 44. Proximity sensors such as proximity sensors S1 and S2 may output positive signals when ear bud 24 is inserted into ear 50. Sensor S1 may be a tragus sensor and sensor S2 may be a concha sensor or sensors such as sensors S1 and/or S2 may be mounted adjacent to other portions of ear 50. Sensors S3 and S4 may be located away from ear 50, so that sensors S3 and S4 output negative signals when ear bud 24 is inserted into ear 50.

The status of sensors S1, S2, S3, and S4 may be analyzed to help discriminate between possible usage scenarios for ear buds 24 (e.g., an ear bud is in a protective case, an ear bud is in a user's pocket, an ear bud is being held by the fingers of a user as the user is inserting the ear bud into ear 50, ear bud 24 is in ear 50, etc.). Based on this status information, appropriate action can be taken by ear buds 24 and electronic device 10.

Figure 4:
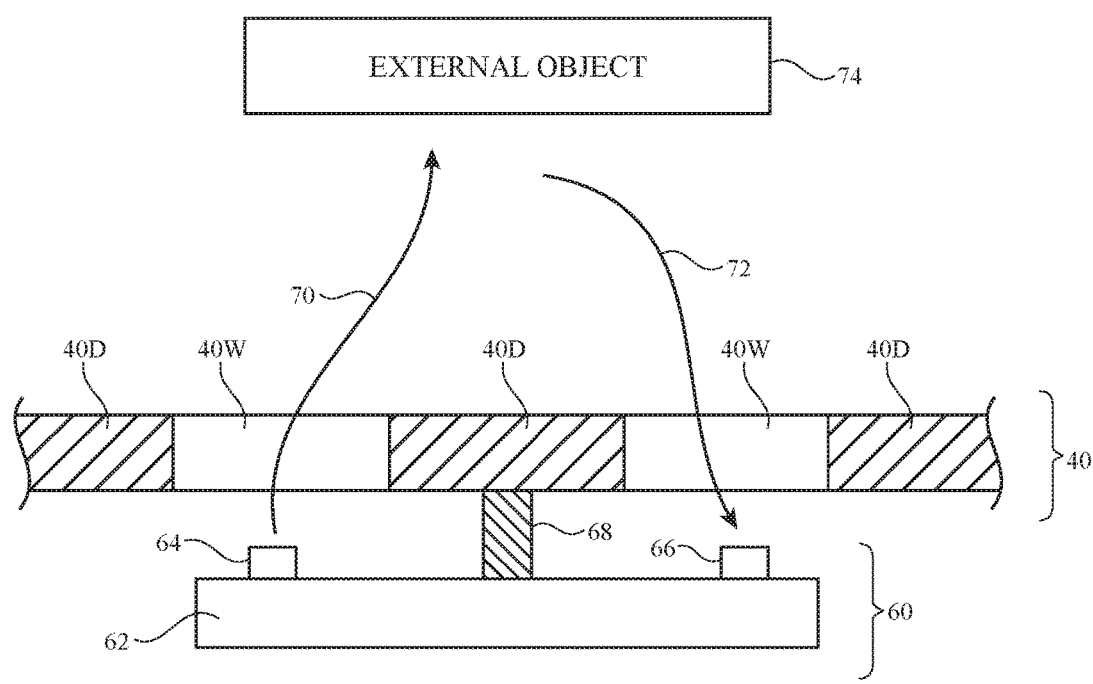
FIGS. 4, 5, and 6 are cross-sectional side views of portions of housing wall structures for ear buds and associated light-based proximity sensors in accordance with an embodiment.

With one illustrative arrangement, proximity sensors in ear buds 24 may be formed using light-based proximity sensors. An illustrative light-based proximity sensor that has been mounted within housing 40 of ear bud 24 is shown in FIG. 4. As shown in the cross-sectional side view of FIG. 4, light-based proximity sensor 60 may have a substrate such as substrate 62. Substrate 62 may be formed from a rigid printed circuit board (e.g., substrate 62 may be formed from fiberglass-filled epoxy or other rigid printed circuit board material) or may be a flexible printed circuit (e.g., substrate 62 may be formed from a flexible layer of polyimide or a sheet of other flexible polymer). Components may be mounted on substrate 62 for handling proximity sensor signals. These components may include light source 64 and light detectors 66.

Light source 64 may be a light-emitting diode such as an infrared light-emitting diode that emits light 70 that is out of the visible spectrum (e.g., to avoid distracting the user). Light detector 66 may be a photodetector based on a phototransistor or photodiode and may be sensitive to the wavelength of light 70. In the absence of ear 50 or other external object such as external object 74 (e.g., a user's finger, the interior of a pocket, a table top, etc.), light 70 will travel into free space and will not be reflected towards detector 66. As a result, the output of sensor 60 will be negative. In the presence of ear 50 or other external object 74, however, reflected light 72 from external object 74 will be detected by detector 66. The output of sensor 60 in this situation will therefore be positive. Light 70 (and reflected light 72) may be visible light, infrared light, broad spectrum light, narrow spectrum light (e.g., light having a spectral width of less than 20 nm or less than 5 nm), may be ultraviolet light, or may be other suitable light.

Sensor 60 may be mounted behind a portion of housing wall 40. In the illustrative configuration of FIG. 4, portions 40D of housing wall 40 are different than portions 40W of housing wall 40. Portions 40D may absorb light 70 and may therefore reduce the signal-to-noise ratio of reflected signal 72. To enhance the signal-to-noise ratio of proximity sensor 60, infrared-transparent materials may be used in forming windows in housing 40. For example, portions 40W may be infrared-transparent materials (e.g., plastic, glass, etc.), may be portions of housing 40 that include microperforations to enhance infrared light transmission (e.g., laser-drilled openings with diameters of less than 75 microns, more than 50 microns, less than 150 microns, or other suitable sizes), or may be other material or structures for enhancing the transmission of light 70 and the transmission of reflected light 72.

Figure 5:
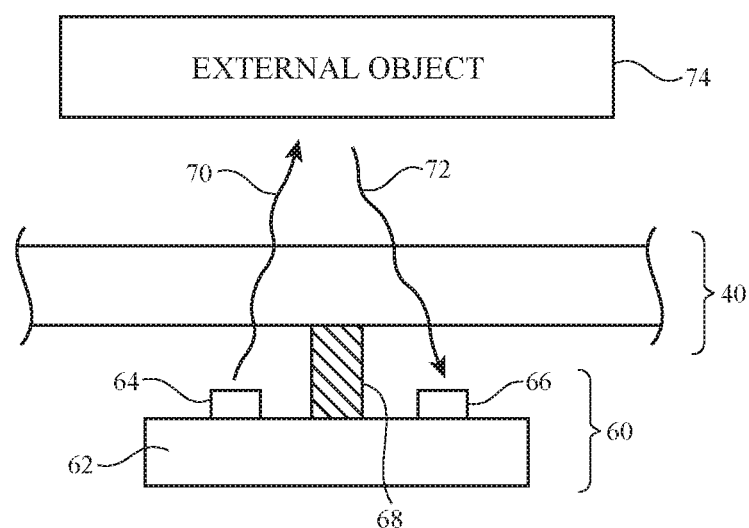

Some of light 70 may scatter when emitted by light source 64, so an optional light blocking structure such as structure 68 may be incorporated into sensor 60, if desired. Structure 68 may be formed from opaque plastic, metal, or other opaque materials. Structure 68 may be formed as an integral portion of housing 40, may be a molded plastic member on substrate 62, may be a member that is attached to substrate 62 using adhesive or other suitable mounting arrangements, or may be any other light blocking structure. Clear polymer or other material may be interposed between light source 64 and housing 40 and may be interposed between housing 40 and light detector 66. The illustrative configuration of FIG. 5, which does not include any polymer or other material between the circuitry of sensor 60 and the inner surface of housing 40, is shown as an example.

Figure 6:
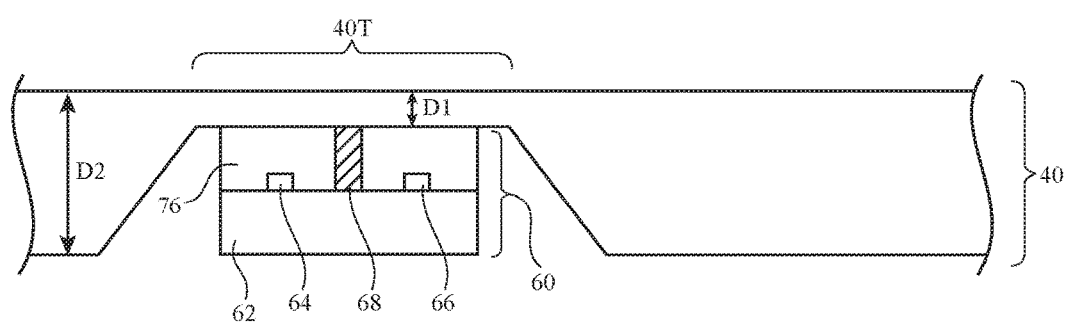

FIG. 6 is a cross-sectional side view of housing 40 and sensor 60 in an illustrative configuration in which a portion of housing 40 has been locally thinned to enhance light transmission for sensor 60. Housing 40 has a thickness of D2 in regions of ear bud 24 that are not aligned with sensor 60. In portions of housing 40 that are aligned with sensor 60, housing 40 is locally thinned and has a thickness D1 that is less than D2. The value of D2 may be 450 microns, more than 300 microns, more than 700 microns, less than 2 mm, or other suitable thickness. The value of D1 may be 150 microns, more than 100 microns, less than 400 microns, or other suitable thickness). Illustrative polymer 76 (e.g., infrared-transparent polymer) or other structures may be placed between substrate 62 and the inner surface of thinned portion 40T of housing 40 to help secure sensor 60 to ear bud 24 or other mounting techniques may be used.

Figure 7:
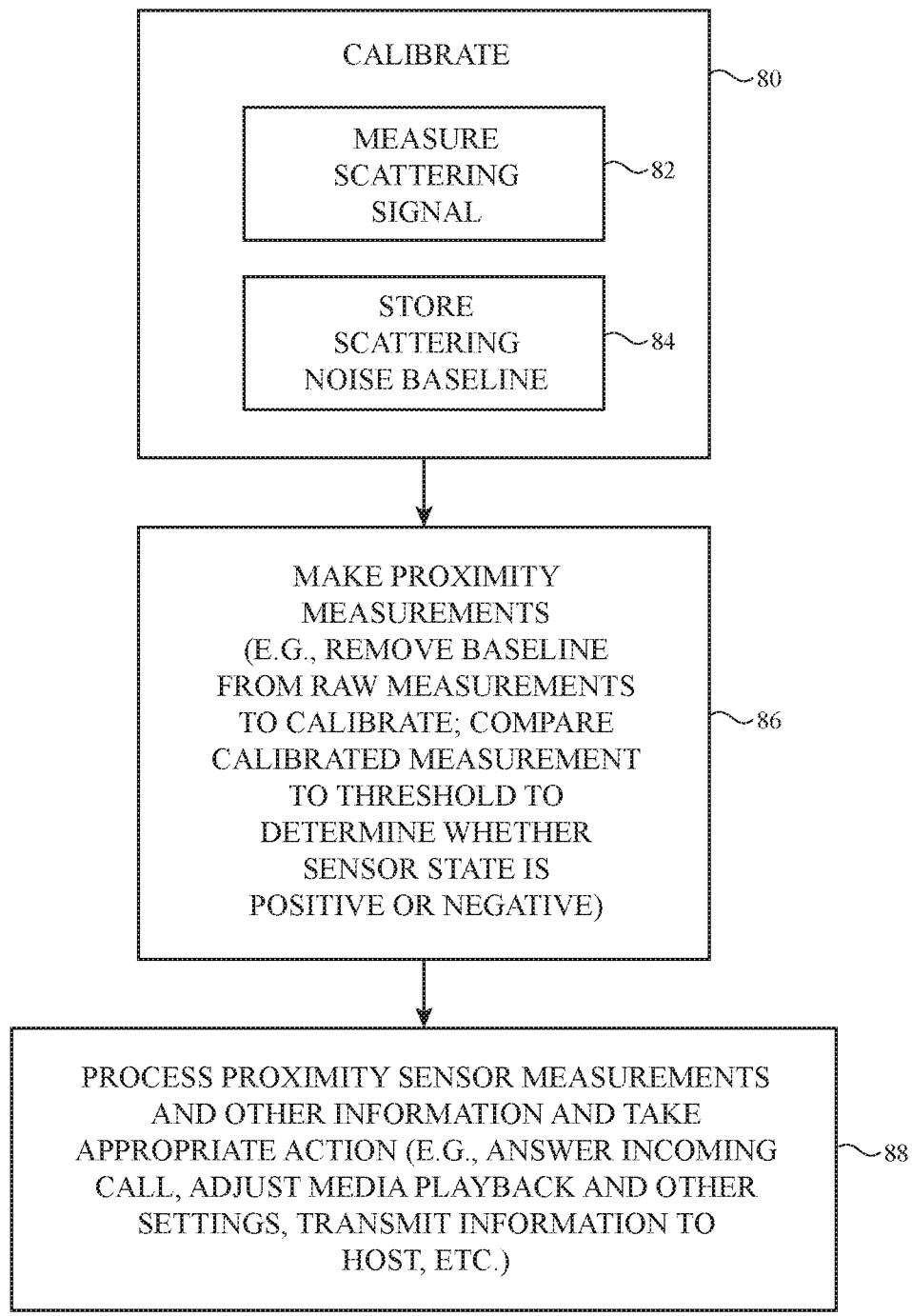
FIG. 7 is a flow chart of illustrative steps involved in calibrating and operating wearable electronic devices such as wireless ear buds in accordance with an embodiment.

Some of light 70 may be scattered into detector 66 by particles or other substances in housing 40. Calibration operations may be performed during manufacturing or during use of ear bud 24 by a user to remove this source of noise from the proximity detector signal produced by sensor 60. Illustrative steps involved in the calibration and use of proximity sensor data in ear buds 24 is shown in FIG. 7. During calibration operations (step 80), the amount of light 70 that is being scattered back towards detector 66 by housing 40 rather than being reflected back towards detector 66 by an external object can be ascertained. In particular, the amount of light 70 that is scattered rather than being transmitted may be measured at step 82. For example, light source 64 may be modulated using a square wave or other suitable modulating signal in the absence of an external object. When light source 64 is turned on, detector 66 can measured the scattered light signal from housing 40. When light source 64 is turned off, detector 66 will measure background signals. Using this technique, the amount of scattered light in sensor 60 (e.g., a fraction of the amount of transmitted light 70) may be determined and stored in control circuitry 30 for use as calibration data (see, e.g., step 84).

At step 86, after the calibration operations of step 80 have been performed, ear bud 24 may be used by a user while data is gathered from proximity sensors S1, S2, S3, and S4 and other sensors and circuitry in ear buds 24. The user may store ear buds 24 in a protective charging case (e.g., a case having a connector that mates with a corresponding connector on stem 40-2 or other portion of ear bud 24 to facilitate battery recharging operations), may store ear buds 24 in a pocket of an article of clothing or a bag, may allow ear buds 24 to rest on a surface such as a table top, may pick up and hold ear buds 24 by body 40-1 and/or stem 40-2, may insert ear buds 24 into ears 50, and may remove ear buds 24 from ears 50.

In each of these different possible usage scenarios, there is a potential for a different set of sensors to be blocked and a potential for a corresponding different set of sensors to be unblocked. The amounts of time that the sensors are blocked and unblocked will also generally vary in different scenarios.

Sensors may be blocked by ears 50, by a user's fingers, by a portion of a pocket of a case or article of clothing, by a table surface of other resting surface, etc. For example, if sensors S1 and S2 are positive and sensors S3 and S4 are negative, ear buds 24 and device 10 can conclude that ear buds 24 have been inserted into ears 50 (i.e., sensors S1 and S2 are now resting adjacent to ear 50 and sensors S3 and S4 are uncovered because the user's fingers have released the stems of ear buds 24). If sensors S1, S2, S3, and S4 are all negative (as another example), it can be concluded that ear buds 24 are in an enclosed area such as the interior of a pocket.

Accelerometer data from accelerometer 38 and/or other information (e.g., information from microphone 36) may be used to help accurately identify usage scenarios. As an example, if accelerometer 38 indicates that ear buds 24 are not moving, it can be concluded that ear buds 24 are resting on a table or other non-moving surface. If accelerometer 38 indicates that ear buds 24 are moving, it can be assumed that ear buds 24 are not resting on a table. Clock data (e.g., time information, date information, etc.) may be used in conjunction with sensor data, communications status data (e.g., whether an incoming cellular telephone is being received by device 10), and other information to determine which actions should be taken by ear buds 24 and device 10.

At step 88, ear buds 24 and/or device 10 of FIG. 1 may take suitable action based on the detected state of ear buds 24. For example, if it is determined that a user has just placed one of ear buds 24 into ear 50 in response to an incoming cellular telephone call to device 10, audio playback may be transferred from device 10 to that ear bud. A remote wireless link (e.g., a cellular telephone link with a wireless base station in a cellular telephone network) may be handled by device 10. A local wireless link (link 26 of FIG. 1) may be established between device 10 and ear bud 24 to allow ear bud 24 to transmit and receive audio. If it is determined that ear buds 24 are located in the pocket of a user when an incoming call is received on device 10, the incoming call can be routed to the speaker and microphone of device 10.

In yet another scenario, a user may be using ear bud 24 in ear 50 to handle a cellular telephone call. A local wireless link (link 26) between ear bud 24 and device 10 may be used to transmit microphone and speaker audio signals between device 10 and ear bud 24. Device 10 may maintain a cellular telephone link with remote network equipment. If a user removes ear bud 24 from ear 50 during the telephone call, the microphone and speaker of device 10 can be switched into use so that the telephone call can be sustained even though the user is no longer using ear bud 24.

In some situations, the output of sensor S1 may be positive while sensors S3 and S4 are negative, indicating that ear bud 24 is in ear 50. During media playback, audio may be streamed from device 10 to ear bud 24 and presented to the user with the speaker in ear bud 24. Sensors S3 and S4 may be used as touch buttons. A user can momentarily block one or both of these sensors to advance a track, to pause a track that is currently playing, or to otherwise control media playback. As this example demonstrates, temporarily unused proximity sensors can serve as input devices.

Figure 8:
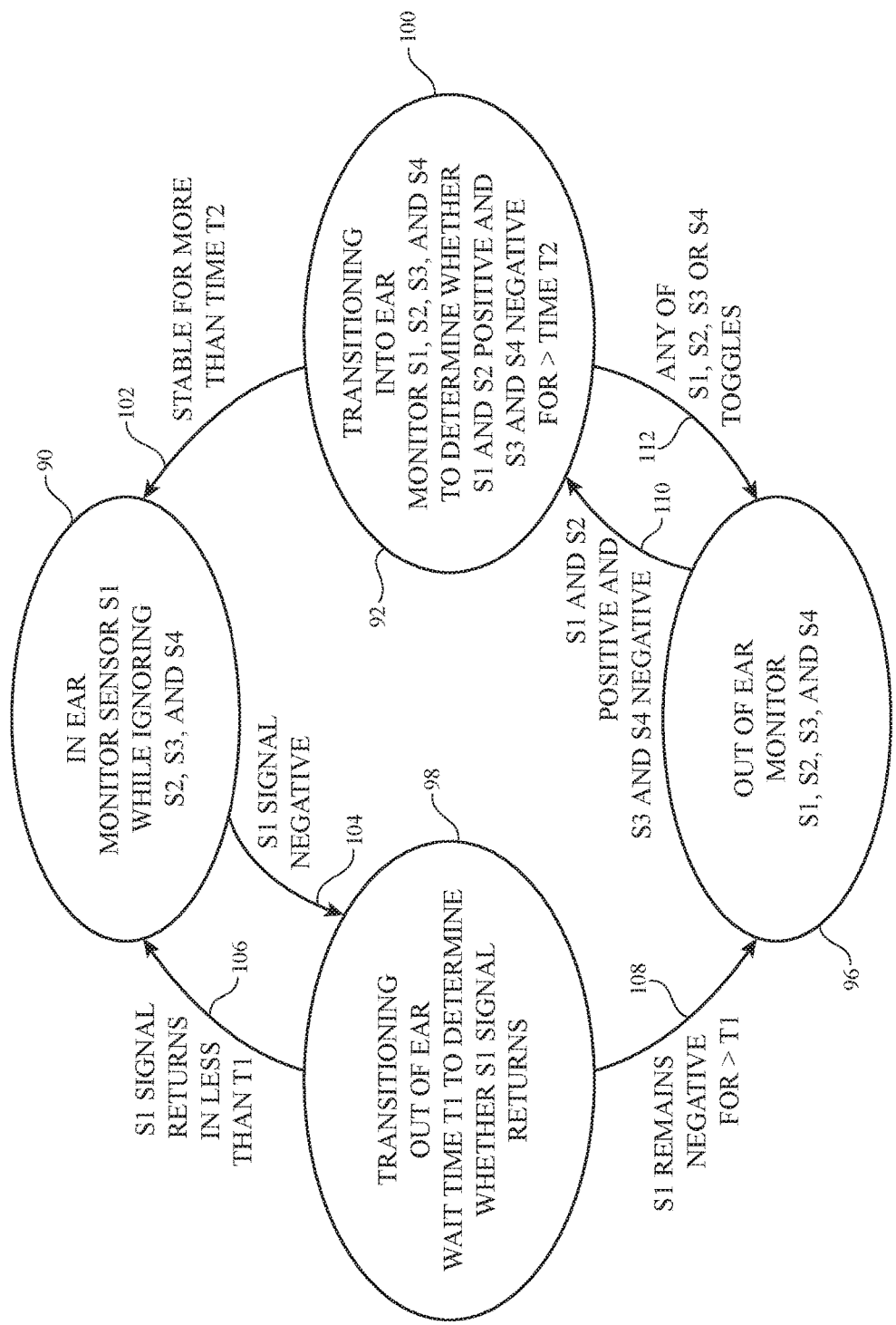
FIG. 8 is a state diagram showing illustrative operations involved in determining the current state of wireless ear buds in accordance with an embodiment.

To discriminate between different usage states, control circuitry 28 and/or control circuitry 16 may analyze sensor data from each of the proximity sensors in ear buds 24 and/or the sensors and other circuitry of ear buds 24 and device 10. An illustrative state diagram showing the operation of the system of FIG. 1 in different states is shown in FIG. 8. Control circuitry 28 and/or control circuitry 16 may determine the current operating state of the FIG. 1 system (e.g., ear buds 24 and/or device 10) by analyzing the output of sensors S1, S2, S3, and S4 and, if desired, additional sensors and sources of operational state information in ear buds 24 and device 10.

In state 96, ear bud 24 is not in ear 50. While ear bud 24 is out of the user's ear, the status of sensors S1, S2, S3, and S4 may be monitored. So long as S1 and S2 are not positive while S3 and S4 are negative, it can be concluded that ear bud 24 is remaining out of the user's ear (i.e., in state 96). Monitoring of S1, S2, S3, and S4 may therefore continue.

In response to detecting a positive output from sensors S1 and S2 and a negative output from sensors S3 and S4, it can be tentatively concluded that ear bud 24 has been placed in ear 50 in a configuration of the type shown in FIG. 3 and that the user has released stem 40-2. Operations may therefore transition to state 92 (a state representing the transition of ear bud 24 into ear 50), as indicated by line 110. During state 92, the status of sensors S1, S2, S3, and S4 can be monitored to determine whether the positive state of sensors S1 and S2 and the negative state of sensors S3 and S4 will be sustained for a threshold amount of time (time T2). The value of T2 may be 0.5 seconds, more than 0.3 seconds, less than 1 second, or other suitable length of time. If any of the outputs of sensors S1, S2, S3, and S4 changes during state 92, it can be concluded that ear bud 24 is not in ear 50 and operations may transition back to state 96, as indicated by line 112.

If sensors S1 and S2 remain positive and sensors S3 and S4 remain negative for time T2, it can be concluded that ear bud 24 is in ear 50 and operations can transition to state 90, as indicated by line 102. During the monitoring operations of state 90, the status of sensor S1 (the tragus sensor) or sensor S2 (the concha sensor) can be monitored and the status of sensors S3 and S4 can be ignored. After ear bud 24 has been placed in ear 50, a user may move in a way that causes sensors S3 and S4 to produce a positive output (e.g., due to the presence of hair, a hat, or other obstructions). The output of sensors S3 and S4 is therefore not necessarily representative of the status of ear bud 24 during use of ear bud 24 and can be ignored when monitoring the sensors to determine the current operating state of ear bud 24. Sensors such as sensors S1 and S2 are immediately adjacent to the user's ear and are therefore more representative of whether or not ear bud 24 is in the user's ear. With one illustrative configuration, sensor S1 may be monitored and sensor S2 may be ignored along with sensors S3 and S4 (e.g., because sensor S1 is more representative of whether or not ear bud 24 is present in ear 50). Other sensor monitoring schemes may be used during state 90, if desired (e.g., schemes in which S2 is monitored but not S1, schemes in which S1 and S2 are monitored, schemes in which S1 and S2 are both monitored but are weighted unequally and/or are filtered using different time-dependent filters, etc.). The arrangement of state 90 of FIG. 8 is an example.

In a scenario in which sensor S1 is being monitored during state 90 while the outputs of sensors S2, S3, and S4 are being ignored, any transition in the state of the output of sensor S1 from positive to negative indicates that ear bud 24 is potentially being removed from ear 50. Operations may therefore transition to state 98, as indicated by line 104.

During the operations of state 98, ear bud 24 is believed to be transitioning out of ear 50. In response to determining during the operations of step 98 that the S1 sensor output has returned to positive before reaching time T1, operations may transition back to state 90, as indicated by line 106 (i.e., it can be concluded that ear bud 24 is still in ear 50). The value of T1 may be 0.25 seconds, less than 1 second, more than 0.1 second, or other suitable amount. The value of T1 may be less than the value of T2 or may be more than the value of T2. If the output of sensor S1 remains negative for a predetermined threshold amount of time (e.g., more than time T1), it can be concluded that ear bud 24 is out of ear 50 and operations can transition to state 96.

Information from the monitoring operations and analysis operations of FIG. 8 can be used to determine which actions to take during the operations of step 88 (FIG. 7). If desired, other sensor data (e.g., accelerometer output), cellular telephone call status information (incoming call present, current call active, etc.), and/or other communications status information and operating status information may be used in determining which actions to take. The user of proximity sensor output information from sensors S1, S2, S3, and S4 is merely illustrative.

The foregoing is merely illustrative and various modifications can be made by those skilled in the art without departing from the scope and spirit of the described embodiments. The foregoing embodiments may be implemented individually or in any combination.

What is claimed is:

1. A wireless ear bud, comprising:
    a housing configured to be placed in a user's ear;
    a speaker in the housing;
    a concha sensor in the housing, wherein the concha sensor emits light that is reflected off of a concha of the user's ear and receives the light that is reflected off of the concha of the user's ear while the housing is in the user's ear, and wherein the concha sensor produces a first output in response to the received light;
    a tragus sensor in the housing, wherein the tragus sensor emits light that is reflected off of a tragus of the user's ear and receives the light that is reflected off of the tragus of the user's ear while the housing is in the user's ear, and wherein the tragus sensor produces a second output in response to the received light;
    control circuitry in the housing that monitors the first and second outputs, wherein, in response to both the first and second outputs being positive for a predetermined period of time, the control circuitry stops monitoring the first output and only monitors the second output; and
    an accelerometer in the housing that is configured to produce an accelerometer output indicative of movement of the housing.

2. The wireless ear bud defined in claim 1 wherein the concha and tragus sensors each have an infrared light-emitting diode and each have a light detector.

3. The wireless ear bud defined in claim 2 wherein the housing comprises a wall and wherein the infrared light-emitting diodes in the concha and tragus sensors emit infrared light that passes through the wall.

4. The wireless ear bud defined in claim 1, wherein the wireless ear bud has a current operating state, and wherein the
    control circuitry is configured to determine the current operating state by analyzing the first and second outputs from at least the concha and tragus sensors.

5. The wireless ear bud defined in claim 4 wherein the control circuitry is further configured to determine the current operating state by analyzing the accelerometer output from the accelerometer.

6. The wireless ear bud defined in claim 5 wherein the concha and tragus sensors include respective infrared light-emitting diodes.

7. The wireless ear bud defined in claim 6 wherein the housing has a first portion that is configured to be inserted into an ear and a second portion that extends from the first portion, wherein the first portion has infrared-transparent portions, and wherein the infrared light from the infrared light-emitting diodes passes through the infrared-transparent portions.

8. The wireless ear bud defined in claim 7 wherein the infrared-transparent portions comprise plastic and wherein the concha sensor is configured to detect infrared light that has reflected off of the concha of the user's ear.

9. The wireless ear bud defined in claim 1 wherein the housing has a first portion that is configured to be inserted into the user's ear and a second portion that extends from the first portion, the wireless ear bud further comprising an infrared light-based proximity sensor in the second portion.

10. An ear bud, comprising:
    control circuitry;
    wireless circuitry that the control circuitry uses to communicate wirelessly with an electronic device;
    a housing having a main body portion that is configured to be inserted into an ear of a user and a stem portion that extends from the main body portion;
    a speaker in the main body portion;
    a first proximity sensor on the main body portion that monitors whether the first proximity sensor is adjacent to the ear; and
    a second proximity sensor on the stem portion, wherein when the main body portion is in the ear, the first proximity sensor produces a positive output indicating that the first proximity sensor is adjacent to the ear and the second proximity sensor produces a negative output indicating that no external object is adjacent to the second proximity sensor, wherein the control circuitry monitors the outputs of the first and second proximity sensors, and wherein, after the first proximity sensor has produced the positive output and the second proximity sensor has produced the negative output for a predetermined period of time, the control circuitry determines that the main body portion is in the ear and stops monitoring the output of the second proximity sensor.

11. The ear bud defined in claim 10 wherein the first proximity sensor is a light-based proximity sensor.

12. The ear bud defined in claim 11 wherein the second proximity sensor is a light-based proximity sensor.

13. The ear bud defined in claim 12 wherein the first and second proximity sensors each include an infrared light-emitting diode and wherein the infrared light-emitting diodes produce infrared light that passes through the housing, the ear bud further comprising an accelerometer in the housing.

14. An ear bud, comprising:
    a housing having a main body portion configured to be inserted into an ear of a user and a stem portion that extends from the main body portion;
    a speaker in the main body portion;
    control circuitry in the housing; and
    at least two proximity sensors on the housing, wherein the proximity sensors comprise:
        a first proximity sensor on the stem portion that emits light away from the user to produce a negative output when the main body portion is inserted into the ear of a user, wherein the control circuitry monitors the first proximity sensor for the negative output; and a second proximity sensor on the main body portion that emits light onto the user to produce a positive output when the main body portion is inserted into the ear of the user, wherein the control circuitry monitors the second proximity sensor for the positive output, and wherein, in response to the first proximity sensor producing the negative output for a predetermined period of time and the second proximity sensor producing the positive output for the predetermined period of time, the control circuitry stops monitoring the first proximity sensor and only monitors the second proximity sensor.

15. The ear bud defined in claim 14 wherein the proximity sensors further comprise:

a third proximity sensor on the main body portion; and a fourth proximity sensor on the stem portion.

16. The ear bud defined in claim 14 further comprising:
an accelerometer, wherein the
control circuitry is configured to analyze outputs from the first and second proximity sensors to determine whether the main body portion has been inserted into an ear and that is configured to use the accelerometer to determine whether the housing is moving.

17. The ear bud defined in claim 16 wherein the control circuitry determines that the main body portion has been inserted into the ear when at least the second proximity sensor has the positive output indicating that the ear is adjacent to the second proximity sensor while at least the first sensor has the negative output indicating that no external object is adjacent to the first sensor.

18. The ear bud defined in claim 17 wherein the first and second proximity sensors each have an infrared light-emitting diode that emits infrared light that passes through the housing and each have a light detector.

* * * * *